(12) United States Patent
Baily et al.

(10) Patent No.: US 8,479,573 B2
(45) Date of Patent: Jul. 9, 2013

(54) FLUID LEVEL SENSOR (75) Inventors: Greg Baily, Roath (GB); Alan Beale, Newport (GB)

(73) Assignee: Huntleigh Technology Limited, Luton, Bedfordshire (GB)

(*) Notice: Subject to any disclaimer, the term of this patent is extended or adjusted under 35 U.S.C. 154(b) by 682 days.

(21) Appl. No.: 12/594,456

(22) PCT Filed: Apr. 1, 2008

(86) PCT No.: PCT/GB2008/001148
§ 371 (c)(1),
(2), (4) Date: Feb. 1, 2010

(87) PCT Pub. No.: WO2008/119993
PCT Pub. Date: Oct. 9, 2008

(65) Prior Publication Data
US 2010/0126268 A1    May 27, 2010

(30) Foreign Application Priority Data
Apr. 2, 2007 (GB) .................................. 0706382.9

(51) Int. Cl.
*G01F 23/26* (2006.01)
(52) U.S. Cl.
USPC .......................................... 73/304 C; 73/323
(58) Field of Classification Search
USPC ................. 73/304 C; 604/540–544
See application file for complete search history.

(56) References Cited

U.S. PATENT DOCUMENTS

| | | | | |
|---|---|---|---|---|
| 4,749,988 A * | 6/1988 | Berman et al. | ................. | 340/618 |
| 5,135,485 A * | 8/1992 | Cohen et al. | ..................... | 604/67 |
| 5,945,831 A | 8/1999 | Sargent et al. | | |
| 6,761,067 B1 * | 7/2004 | Capano | ....................... | 73/304 C |
| 6,823,730 B2 * | 11/2004 | Buck et al. | ................... | 73/304 C |
| 7,127,943 B1 * | 10/2006 | Griffiths et al. | ............ | 73/304 C |
| 7,553,306 B1 * | 6/2009 | Hunt et al. | ..................... | 604/543 |
| 2001/0037680 A1 | 11/2001 | Buck et al. | | |
| 2005/0172712 A1 | 8/2005 | Nyce | | |
| 2011/0146399 A1 * | 6/2011 | Burdi et al. | ................. | 73/304 C |

FOREIGN PATENT DOCUMENTS

| | | |
|---|---|---|
| EP | 0 853 950 A | 7/1998 |
| WO | WO 98/57156 A | 12/1998 |
| WO | WO 99/10714 A | 3/1999 |

* cited by examiner

*Primary Examiner* — Hezron E Williams
*Assistant Examiner* — Hoang Nguyen
(74) *Attorney, Agent, or Firm* — Craig A. Fieschko, Esq.; DeWitt Ross & Stevens, S.C.

(57) ABSTRACT

A fluid level sensor to determine the level of fluid into a container used in negative pressure wound therapy. The sensor includes an array of conductive plates to produce electric field lines through the container and fluid within, the plates serving as the plates of a capacitor. The plates (1-4), are located close to the wall of the container, and are connected to a circuit board, electronics and software to determine the fluid level in the container based on the relative changes of capacitance between the plates. The capacitance is converted into a voltage signal representative of the change. The algorithms are designed to check the fluid level over predefined time periods to indicate the fluid level at more than one point and also track the fluid level. The fluid sensor can be used in the vertical, horizontal or other position of the container as desired.

25 Claims, 10 Drawing Sheets

FLUID LEVEL SENSOR

FIELD OF THE INVENTION

The present invention relates to a fluid level sensor, in particular a fluid level sensor to determine the level of fluid or flow rate of fluid into a container used in negative pressure wound therapy. This technique uses a pump to apply negative pressure to a wound in order to remove exudate fluid out of a wound bed and maintain a sub-atmospheric pressure at the wound site.

BACKGROUND OF THE INVENTION

With these pump devices the level of exudate fluid collected in a container must be monitored to ensure the container doesn't become completely filled. This is important to avoid the pump unit from becoming infected and to ensure the correct therapy is being applied. Due to the infectious nature of the exudate fluid and that the containers can be disposable it is a significant advantage to employ a non-contact fluid level detection method.

There are many techniques for measuring fluid levels including floats, contacts, ultrasound and light, but capacitive or electric field sensing has perhaps the most advantages for measuring wound exudate fluid levels. It is known to place conductive elements on the outside of a container connected to a circuit to detect any change in the capacitance of the capacitor formed thereby. The change in capacitance is due to the change in the dielectric constant of the combination of the container and fluid due to change in the fluid level therein. Such sensors are either ON or OFF and detect when the fluid reaches the level of the capacitance element. There is no availability to detect the fluid level at several points within a container or to track the flow of fluid.

The sensors also cannot differentiate between a fluid level within the container or drops spattered across the walls of the container.

Accordingly, the invention seeks to make improvements.

SUMMARY OF THE INVENTION

The present invention provides a capacitance fluid level sensor to determine the fluid level within a container used to receive fluid from a human body, the container connected to means for removing fluids from a human body and a port for entry of fluid into the container, a capacitor formed of a series of conductive plates located outside of the container adjacent to an external wall of the container within a housing, means to sense the relative change in capacitance between the series of conductive plates as the fluid level rises in the container and for generating a signal to indicate fluid level positions within the container.

Unlike the existing devices which only provide a signal indicative of a capacitance value corresponding to a set fluid level, the present invention can provide a signal indicative of different set points within a container and can also differentiate between a fluid level reached and drops spattered on the wall of the container. The relative change between the conductive plates is sharp for spatter in comparison to relative changes between the conductive plates when a fluid level is reached. It is also possible with the invention to change the fluid level points dynamically when different sized containers are used which is not possible with the existing systems.

Preferably, the fluid sensor conductive plates and electronics are attached to an internal surface of housing means accommodating the container, the surface of the conductive plates internally within the housing means shielded from detecting capacitance changes, so that only capacitance changes due to fluid level within the container are detected. Advantageously, a reference conductive plate is provided on the internal surface of the housing located above the container to differentiate from fluid level sensing and the capacitance changes when a nurse or carer handles the device.

Preferably, the fluid level sensor can detect fluid level in the vertical, horizontal or other orientation, of the container.

Preferably, the relative changes of capacitance of between all the plates are detected to provide a continuous measurement of fluid level. Advantageously, this provides a means of fluid level tracking which can indicate a time when a container will become full.

More preferably, the fluid level tracking continuously measures the rate of change of fluid level and more preferably, means are provided to trigger an alarm if the increase in fluid level is over a pre-determined threshold. A 'normal' wound would tend to produce 0-4 ml of exudate an hour, changes in these levels over time are a useful indicator of wound healing progression.

The conductive plates can be of various configurations to provide different levels of accuracy and sensitivity. Preferably, the conductive plates can be formed as thin metal strips so that the capacitance changes between each strip can be detected to provide a more sensitive and more accurate signal of fluid level, spatter and flow rate.

BRIEF DESCRIPTION OF THE DRAWINGS

The invention will now be described by way of example with reference to the following figures:—

DETAILED DESCRIPTION OF PREFERRED VERSIONS OF THE INVENTION

Figure 1:
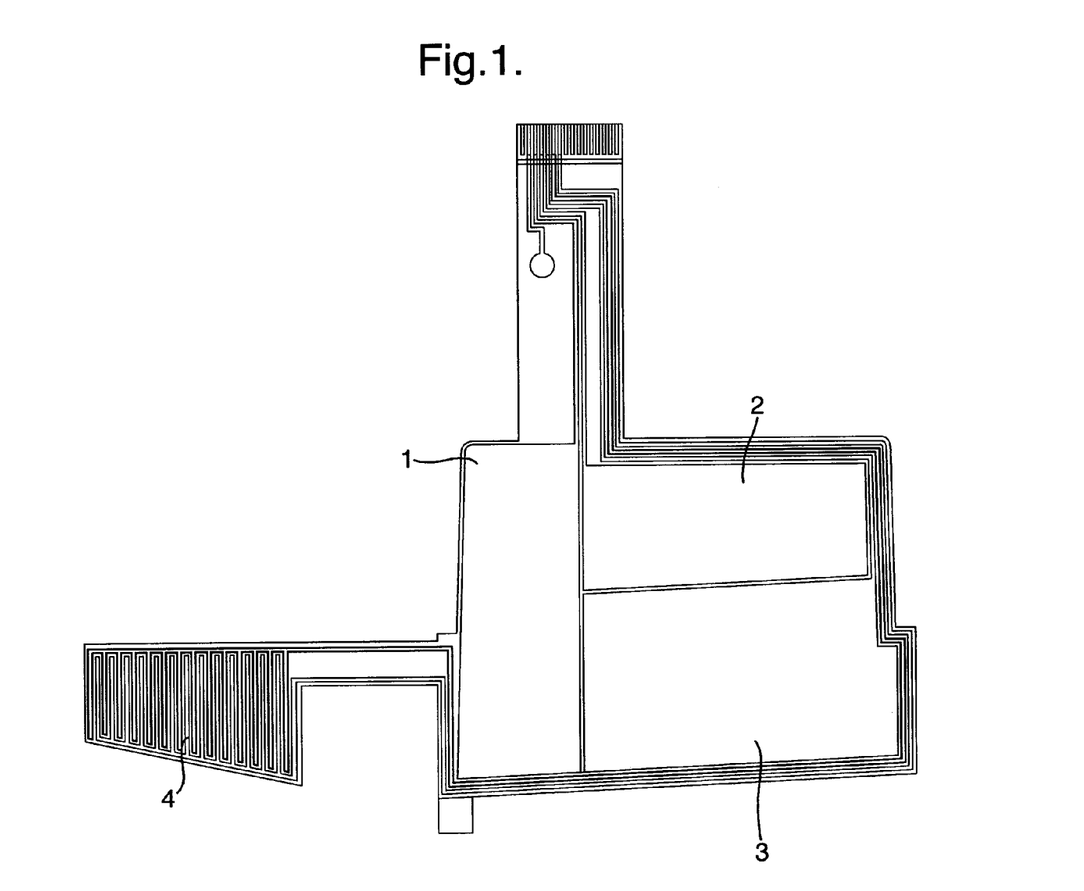
FIG. 1 shows a schematic view of the fluid level sensor according to a preferred embodiment of the invention.
Figure 2:
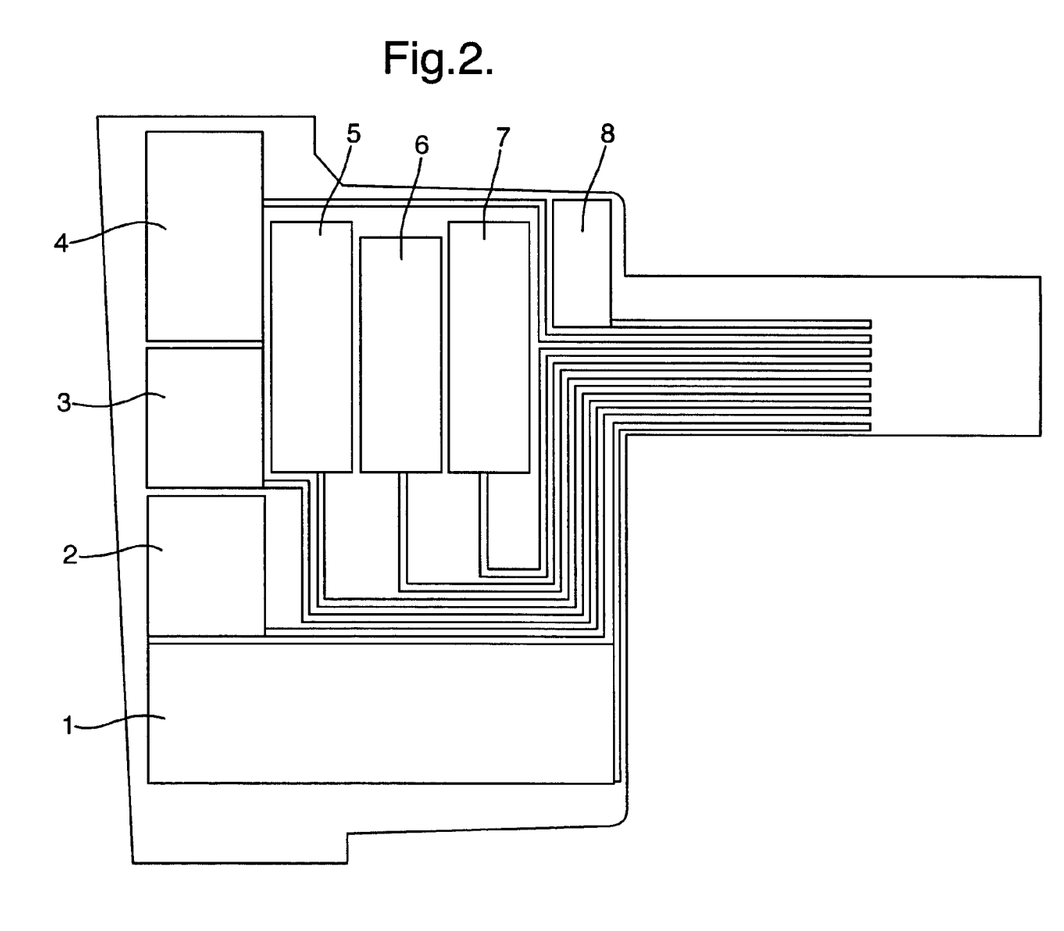
FIGS. 2 to 5 shows alternative arrangements of the fluid level sensor.
Figure 3:
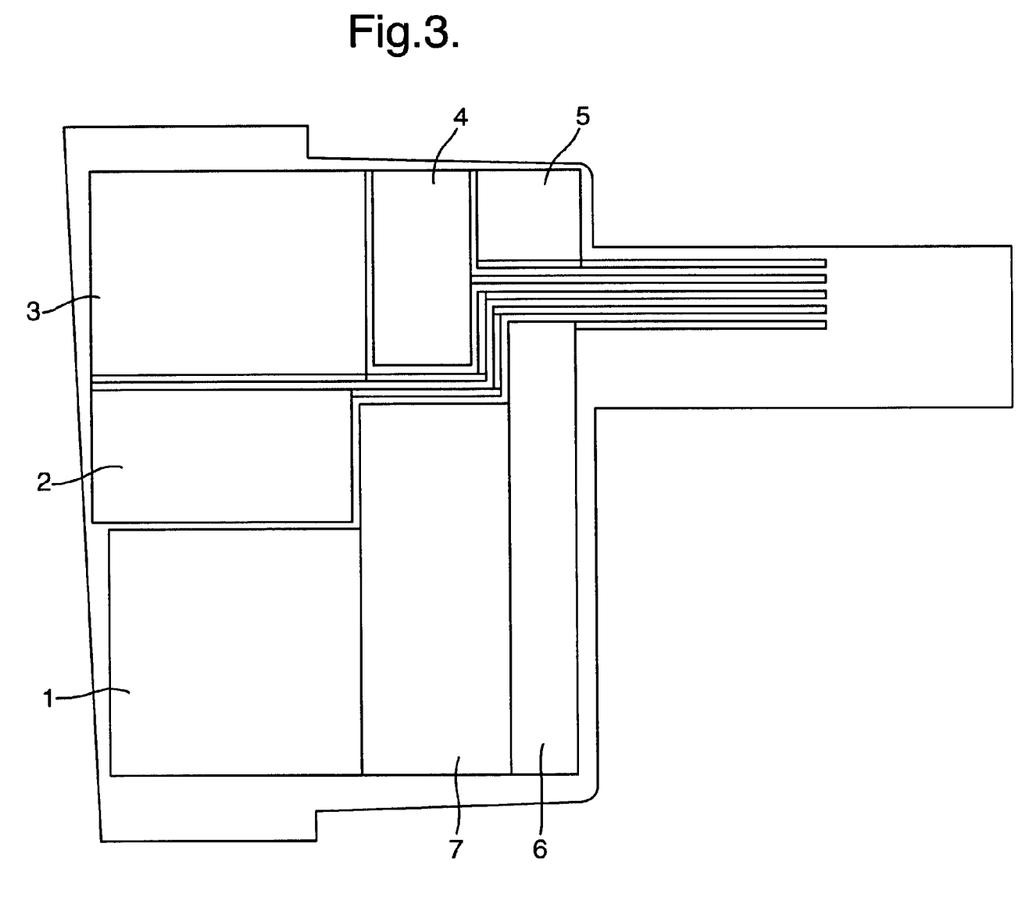
Figure 4:
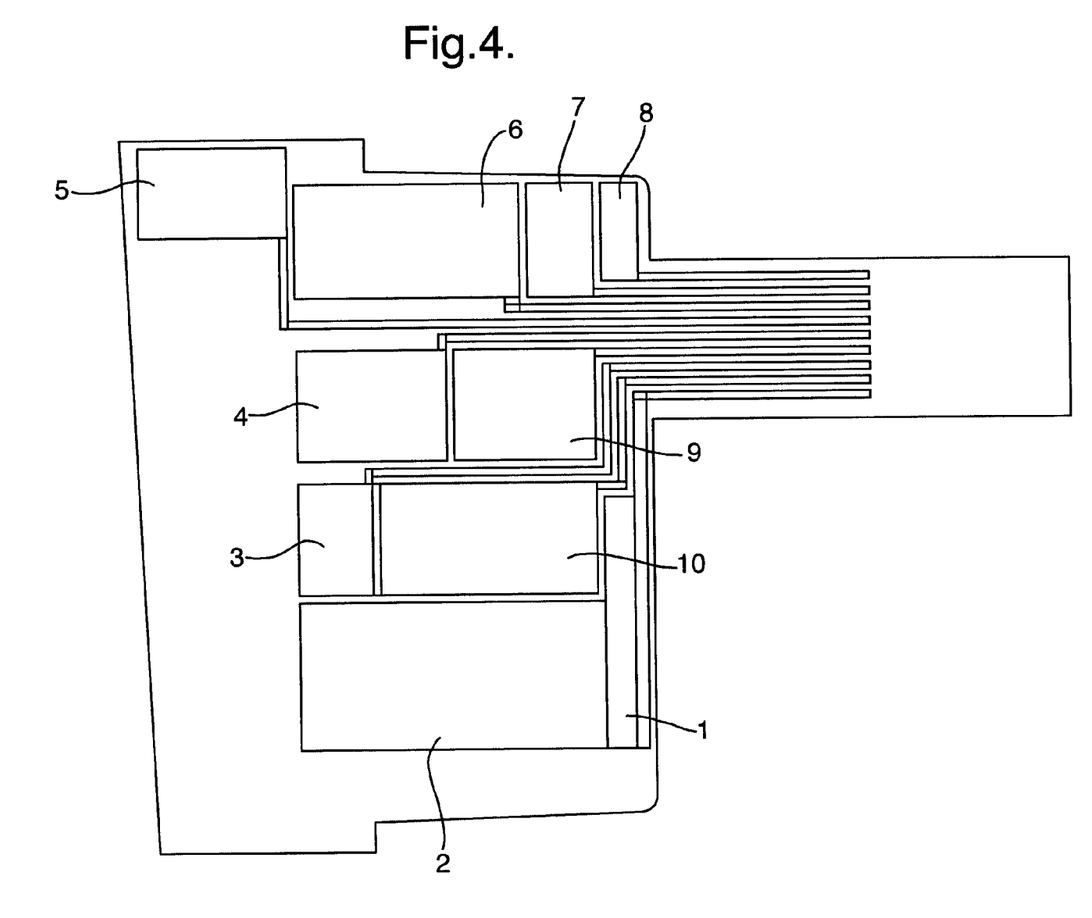
Figure 5:
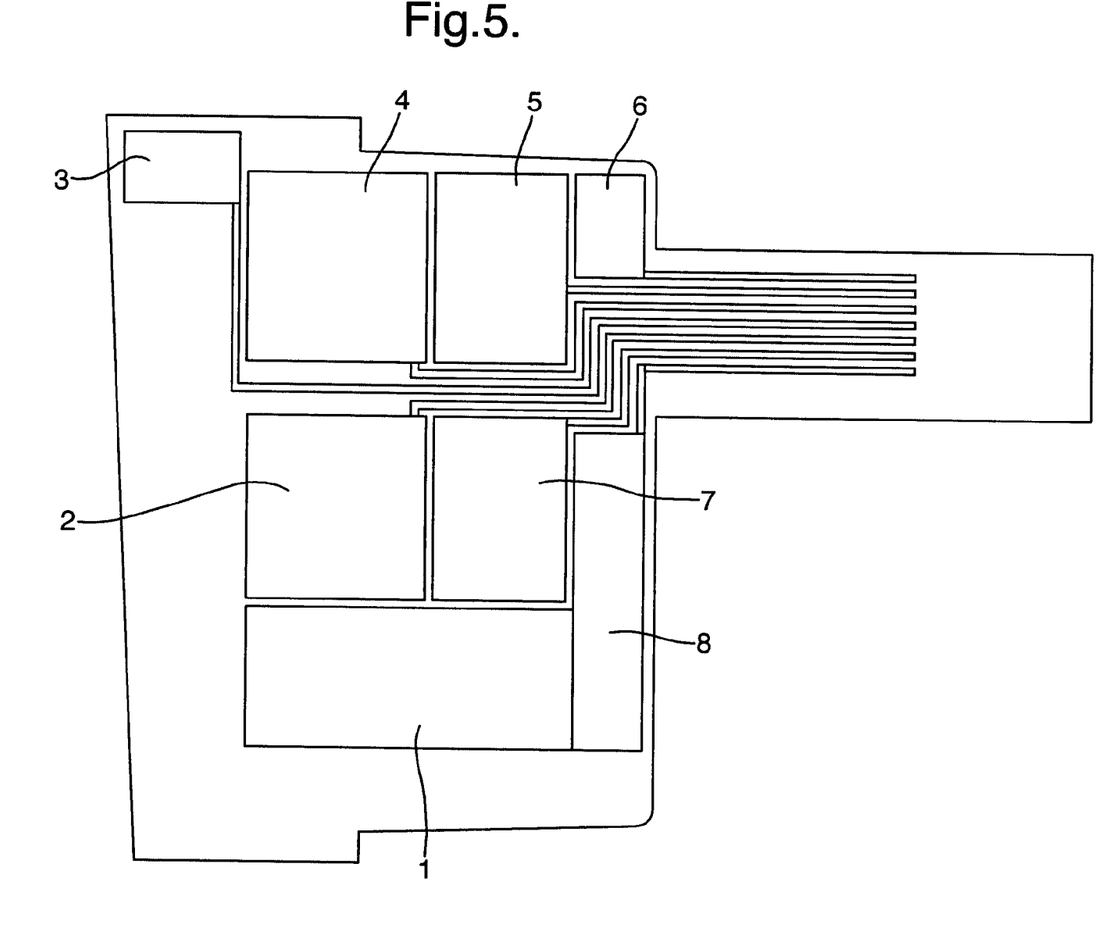

Referring to FIG. 1, the fluid sensor in one preferred embodiment includes an array of conductive plates in a basic layout as shown in the Figure. On the front side of the array are conductive plates 1-4 configured into thin strips. These strips have heights that are designed to cover the container height in both the vertical and horizontal orientations of the container. The conductive strips 1-4 are preferably made from thin flexible metal material and separated from each other by an insulating material. The strips are mounted on a conventional flexible circuit board which is not described in detail.

There is no limit to the number of conductive plates that can be used as illustrated in the different arrangements of the fluid sensor shown in FIGS. 2 to 5. Futhermore, depending on the container size and shape, the conductive plates may even be in the form of thin strips, thin wires or even dots. FIGS. 9*a* to 9*d* show possible variations of the conductive plates. On the reverse side of the circuit board there is a shield plate that covers the conductive plates 1-4, and ensures that the conductive plates only pick up a change in capacitance in front of the array and not behind. There is also a reference plate 4 detects changes in capacitance due to handling of the container rather than fluid level.

The conductive plates 1-4, are of a size to produce electric field lines through the container and fluid within such that the plates serve as the plates of a capacitor. The plates 1-4, are located close to the wall of the container where the fluid levels are to be measured. The fluid sensor arrangement can be located so that it is in contact with the container wall or it could be separated even further, on the wall of the pump housing that draws the fluid through the container. This allows the sensor to be out of sight of the container.

Figure 6:
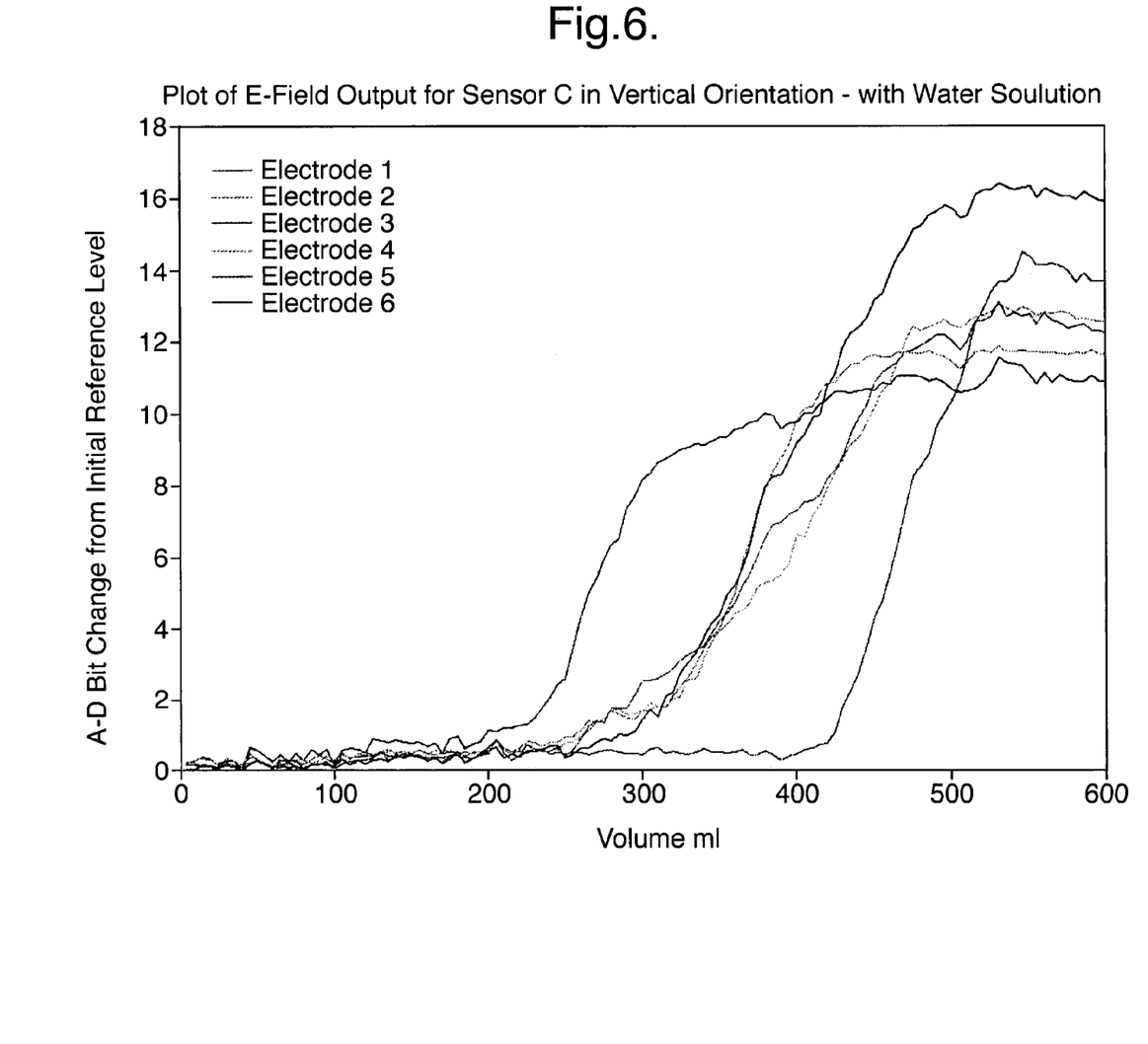
FIG. 6 shows the fluid level sensor output and multiple trigger points with the container in a vertical orientation.
Figure 7:
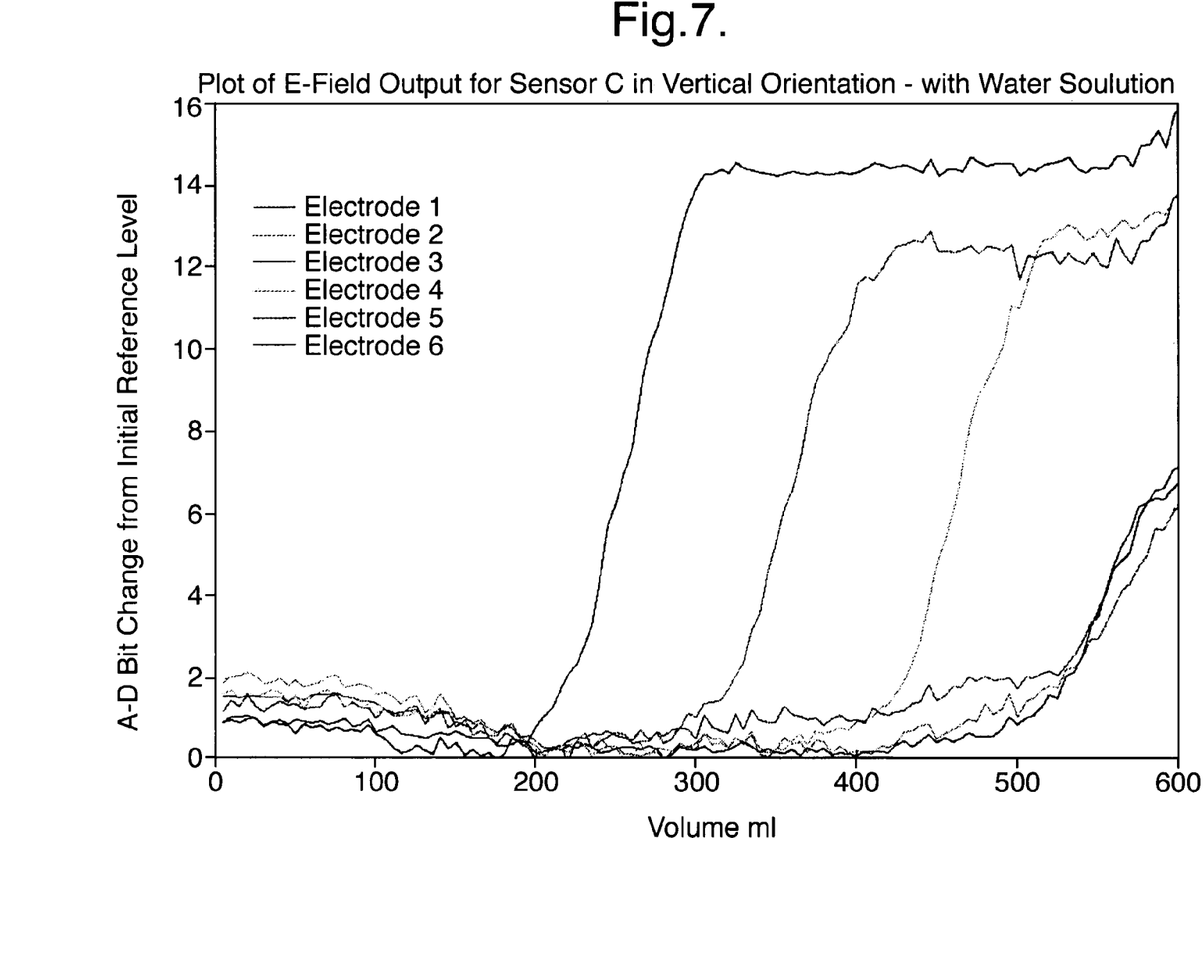
FIG. 7 shows the fluid level sensor output and multiple trigger points with the container in a horizontal orientation.

The conductive plates 1-4 are connected to a circuit board and conventional electronics and software to determine the fluid level based on the relative changes of capacitance between the plates. The capacitance is converted into an electric signal, typically a voltage signal representative of the change. The capacitance changes provide a continuous measure of capacitance level against volume. The algorithms are specifically designed to check the fluid level over predefined time periods. This means that not only can the device indicate fluid level at more than one point and provide an alarm if desired, but it can also track the fluid level. The fluid sensor can be used in the vertical, horizontal or other position of the container as desired. As the fluid level rises in the container, the voltage output from the conductive plates will change, as shown by the traces in FIGS. 6 and 7. In FIGS. 6 and 7, fluid levels are chosen to trigger a fluid level indication or provide an alarm at approximately 400 ml, 450 ml and 500 ml.

The dielectric and other properties of the exudate fluid filling the container can vary from patient to patient, and therefore the conductive plates are arranged to self calibrate their output by comparing the relative changes in capacitance between the plates rather than mean values or values to a reference level. In this way, the different effects of different fluids is cancelled out. Using this ratiometric technique allows greater sensitivity and accuracy than detecting the mean value.

Existing systems only trigger at one point, the present sensor system can provide an indication of more than one level and also provide alarms and can indicate when to turn off the pump to stop fluid from overfilling the container.

If more trigger levels are required it is possible to either add more conductive plates or change the control algorithms.

Figure 8:
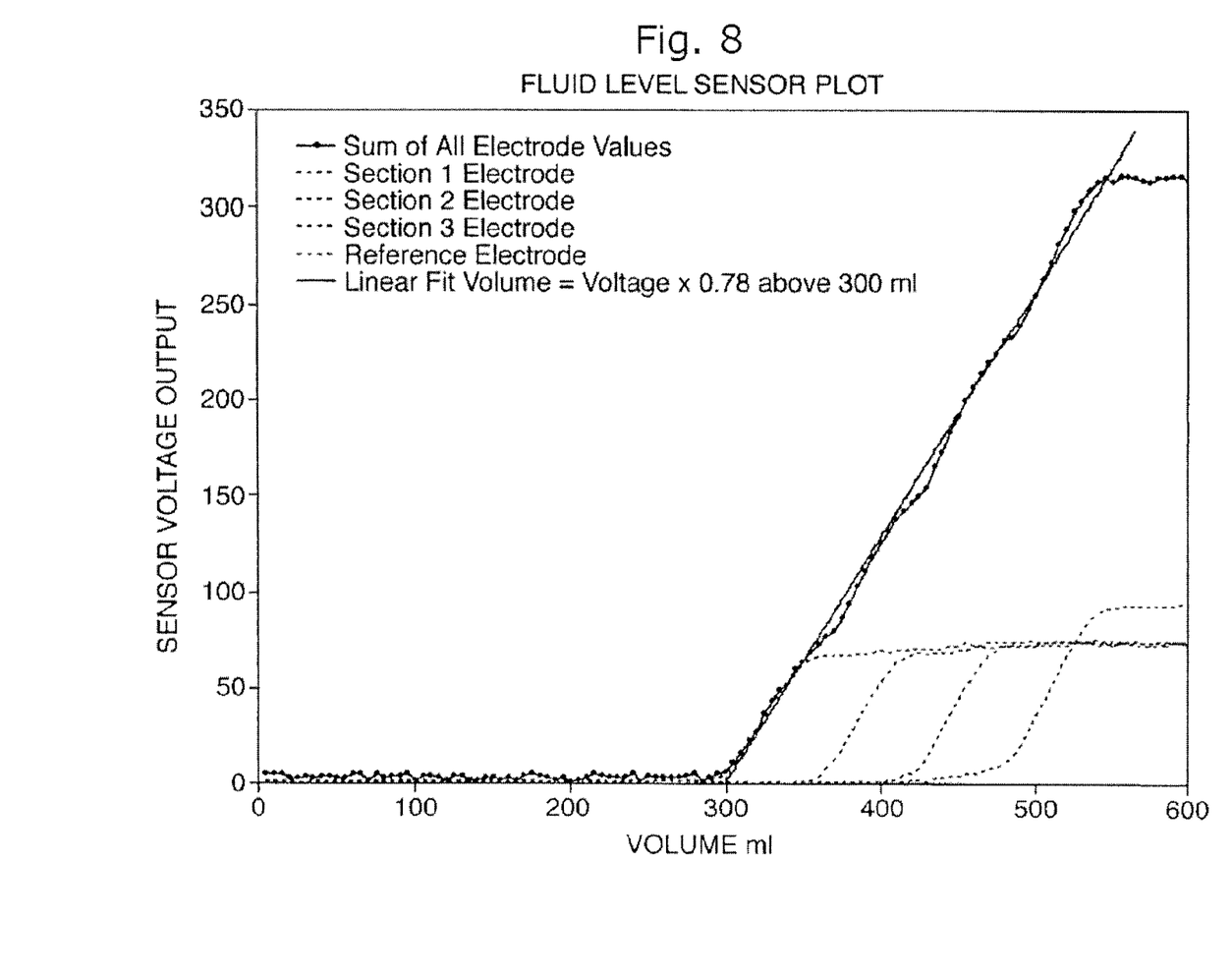
FIG. 8 shows continuous fluid level tracking according to the invention.
Figure 9A:
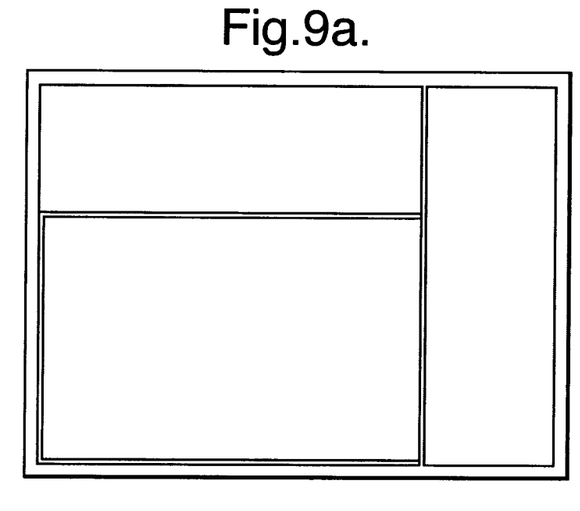
FIGS. 9*a* to 9*d* show different arrangements of conductive plates for the fluid level sensor.
Figure 9B:
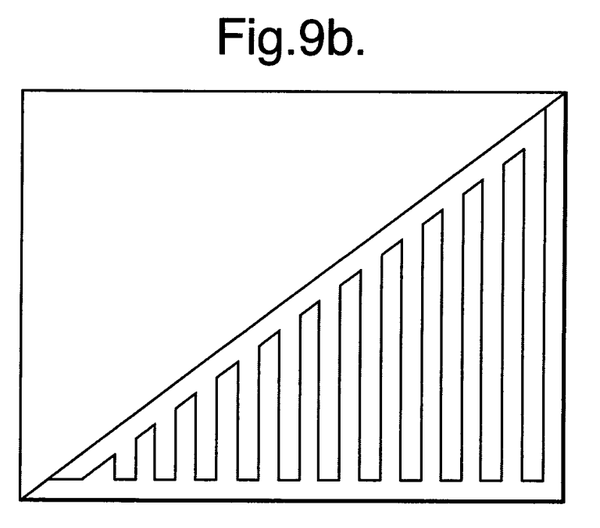
Figure 9C:
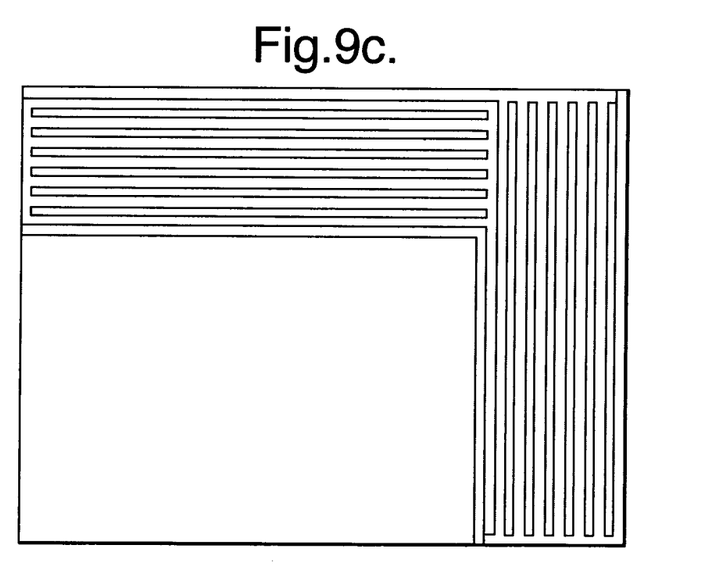
Figure 9D:
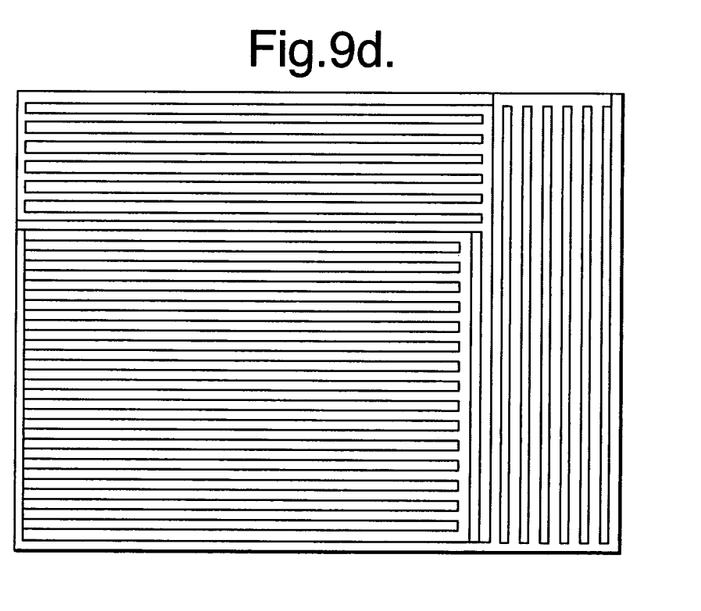

Continuous tracking of the fluid level is shown in FIG. 8. The outputs from all the conductive plates are summed to give a relatively linear relationship between voltage output and volume.

The advantage of the continuous tracking in a wound therapy device is the ability to see whether the exudate level is rising too fast suggesting a deteriorating clinical condition. A 'normal' wound would tend to produce 0-4 ml of exudate an hour, changes in these levels over time are a useful indicator of wound healing progression. It is a potential life saving feature by detecting if blood has started to get into the wound since the rate of fluid level change would be too high.

The sensor software can also help detect splatter and spotting which is caused by Exudate being displaced onto the canister wall adjacent to the sensor by high pressures or initial surges when therapy starts. The sensor software has a state of conditions which when met over predefined timescales to differentiate between splatter or genuine full.

The invention claimed is:

1. A capacitance fluid level sensor to determine the fluid level within a container used to receive fluid from a human body, the container connected to means for removing fluids from a human body and a port for entry of fluid into the container, a capacitor formed of a series of conductive plates located outside of the container adjacent to an external wall of the container, means to sense the relative change in capacitance between the series of conductive plates as the fluid level rises within the container and for generating a signal to indicate fluid level positions within the container, wherein a reference conductive plate is provided on the internal surface of the housing located above the container to differentiate from fluid level sensing and the capacitance changes when a nurse or carer handles the device.

2. The capacitance fluid level sensor as claimed in claim 1 wherein the fluid sensor conductive plates and electronics are attached to an internal surface of housing means accommodating the container, the surface of the conductive plates internally within the housing means shielded from detecting capacitance changes, so that only capacitance changes due to fluid level within container are detected.

3. The capacitance fluid level sensor as claimed in claim 1 wherein the fluid level sensor can detect fluid level in the vertical or horizontal orientation of the container.

4. The capacitance fluid level sensor as claimed in claim 3 wherein the fluid sensor conductive plates extend towards an upper portion of the container to detect a fluid level representing a high level and extending towards a lower portion of the container to represent a lower level, in the vertical orientation of the container.

5. The capacitance fluid level sensor as claimed in claim 3 wherein the fluid sensor conductive plates extend towards an upper portion of the container to detect a fluid level representing a high level and extending towards a lower portion of the container to represent a lower level, in the horizontal orientation of the container.

6. The capacitance fluid level sensor as claimed in claim 1 wherein relative changes of capacitance between all the plates are detected to provide a continuous measurement of fluid level.

7. The capacitance fluid level sensor as claimed in claim 1 wherein the conductive plates are formed as a plurality of conductive metal strips so that the capacitance changes between each strip can be detected to provide a more sensitive and more accurate signal of fluid level, spatter and flow rate.

8. The capacitance fluid level sensor as claimed in claim 7 wherein the conductive plates are formed as a plurality of conductive metal strips positioned generally vertically in parallel and horizontally in parallel.

9. A system for measuring fluid received from a human body, the system including:
   a. a container including a port for entry of fluid into the container;
   b. a set of conductors situated outside the container and adjacent an external wall of the container, wherein at least some of the conductors lack electrically conductive connection therebetween;
   c. a circuit configured to provide signals indicative of changes in capacitance between the conductors; and
   d. a housing wherein the container is fit;
   (i) whereby monitoring of the changes in capacitance provides information regarding the amount of fluid in the container;
   (ii) wherein the conductors are situated on the housing to rest adjacent the external wall of the container when the container is fit within the housing; and
   (iii) wherein at least one of the conductors is situated on the housing above the container.

10. The system of claim 9 further including a vacuum source configured to apply suction to the port, whereby fluid may be pulled from the port into the container.

11. The system of claim 9 wherein the conductors are situated on the external wall of the container.

12. The system of claim 9 wherein:
   a. at least some of the conductors are arrayed in a horizontal direction, and
   b. at least some of the conductors are arrayed in a vertical direction.

13. The system of claim 9 wherein at least some of the conductors are arrayed in spaced relation in a vertical direction.

14. The system of claim 9 wherein:
   a. the container includes a container floor, at least a portion of the container floor being sloped; and
   b. at least some of the conductors are arrayed in spaced relation in a horizontal direction adjacent the sloped portion of the container floor.

15. The system of claim 9 wherein the conductors are at least partially defined by plates, each plate being oriented at least substantially parallel to a wall of the container.

16. The system of claim 9 wherein the conductors include several elongated conductive strips aligned parallel to each other.

17. A system for measuring fluid received from a human body, the system including:
   a. a container including:
      (1) container walls surrounding the container interior, and
      (2) a port opening onto the container interior;
   b. conductors:
      (1) situated outside the container interior,
      (2) arrayed at least substantially parallel to the container walls, and
      (3) defining one or more capacitors;
   c. a circuit:
      (1) in communication with the conductors, and
      (2) configured to provide signals indicative of changes in capacitance; and
   d. a housing configured to receive the container;
   (i) whereby monitoring of the changes in capacitance provides information regarding the amount of fluid in the container;
   (ii) wherein the conductors are situated on the housing to rest adjacent an external wall of the container when the container is fit within the housing; and
   (iii) wherein at least one of the conductors is situated on the housing above the container.

18. The system of claim 17 further including a vacuum source applying negative pressure to the interior of the container.

19. The system of claim 17 wherein the conductors are each dimensioned with:
   a. a conductor area oriented at least substantially parallel to the container walls, and
   b. a conductor thickness oriented at least substantially perpendicular to the conductor area, wherein the conductor thickness is substantially less than the conductor area.

20. The system of claim 19 wherein the conductors include several elongated conductive strips aligned parallel to each other.

21. The system of claim 17 wherein the conductors are situated on the external wall of the container.

22. The system of claim 17 wherein:
   a. the container includes a container bottom at which liquid collects when liquid first enters the container, and an opposing container top; and
   b. at least one of the conductors is situated adjacent the container top.

23. The system of claim 17 wherein:
   a. at least some of the conductors are arrayed in a horizontal direction, and
   b. at least some of the conductors are arrayed in a vertical direction.

24. The system of claim 17 wherein at least some of the conductors are arrayed in spaced relation in a vertical direction.

25. The system of claim 17 wherein:
   a. the container includes a container floor, at least a portion of the container floor being sloped; and
   b. at least some of the conductors are arrayed in spaced relation in a horizontal direction adjacent the sloped portion of the container floor.

* * * * *